United States Patent
Colucci-Mizenko et al.

(10) Patent No.: US 10,864,295 B2
(45) Date of Patent: Dec. 15, 2020

(54) POLYMERIC SPINAL FUSION SYSTEM INCLUDING SPINAL CAGE

(71) Applicant: SABIC Global Technologies B.V., Bergen op Zoom (NL)

(72) Inventors: Lynn Colucci-Mizenko, Niskayuna, NY (US); Andrew Kugler, Albany, NY (US)

(73) Assignee: SHPP Global Technologies B.V., Bergen op Zoom (NL)

( * ) Notice: Subject to any disclaimer, the term of this patent is extended or adjusted under 35 U.S.C. 154(b) by 219 days.

(21) Appl. No.: 15/574,542

(22) PCT Filed: May 19, 2016

(86) PCT No.: PCT/US2016/033311
§ 371 (c)(1),
(2) Date: Nov. 16, 2017

(87) PCT Pub. No.: WO2016/187446
PCT Pub. Date: Nov. 24, 2016

(65) Prior Publication Data
US 2018/0147319 A1    May 31, 2018

Related U.S. Application Data

(60) Provisional application No. 62/163,956, filed on May 19, 2015.

(51) Int. Cl.
*A61L 27/18*    (2006.01)
*A61L 27/44*    (2006.01)
(Continued)

(52) U.S. Cl.
CPC ............ *A61L 27/18* (2013.01); *A61F 2/4455* (2013.01); *A61L 27/443* (2013.01); *A61L 27/446* (2013.01);
(Continued)

(58) Field of Classification Search
CPC ........ A61F 2/44–447; A61F 2002/4415–4495; A61L 2/4455; A61L 27/18; A61L 27/443; A61L 27/446; A61L 27/54
(Continued)

(56) References Cited

U.S. PATENT DOCUMENTS

2006/0247638 A1* 11/2006 Trieu ................. A61B 17/7031
                                                                   606/246
2008/0167686 A1    7/2008 Trieu et al.
(Continued)

FOREIGN PATENT DOCUMENTS

WO      2010100267 A1    9/2010

OTHER PUBLICATIONS

International Patent Application No. PCT/US2016/033311; Int'l Preliminary Report on Patentability; dated Nov. 30, 2017; 9 pages.

*Primary Examiner* — Matthew J Lawson
(74) *Attorney, Agent, or Firm* — BakerHostetler

(57) ABSTRACT

A spinal cage for implantation between two adjacent vertebrae includes a polymer composition that includes a polyetherimide. The polyetherimide includes repeating units of the formula

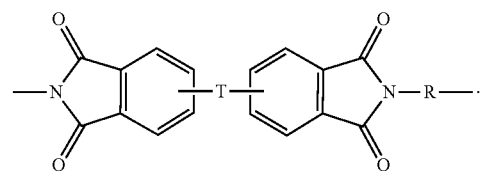

19 Claims, 2 Drawing Sheets

(51) Int. Cl.
  *A61L 27/54* (2006.01)
  *C08G 73/10* (2006.01)
  *A61F 2/44* (2006.01)
  *C08L 79/08* (2006.01)
  *A61F 2/30* (2006.01)

(52) U.S. Cl.
  CPC .......... *A61L 27/54* (2013.01); *C08G 73/1071* (2013.01); *C08L 79/08* (2013.01); *A61F 2/30749* (2013.01); *A61F 2002/3093* (2013.01); *A61F 2002/30153* (2013.01); *A61F 2002/30677* (2013.01); *A61F 2002/30772* (2013.01); *A61F 2310/00011* (2013.01); *A61F 2310/00179* (2013.01); *A61F 2310/00796* (2013.01); *A61L 2300/404* (2013.01); *A61L 2430/38* (2013.01)

(58) Field of Classification Search
  USPC ............................................ 623/17.11–17.16
  See application file for complete search history.

(56) References Cited

U.S. PATENT DOCUMENTS

| | | | |
|---|---|---|---|
| 2009/0234456 A1* | 9/2009 | Nycz | A61F 2/442 623/17.16 |
| 2012/0046750 A1* | 2/2012 | Obrigkeit | A61F 2/4455 623/17.16 |
| 2013/0110241 A1* | 5/2013 | Palmatier | A61F 2/4465 623/17.16 |
| 2013/0158664 A1* | 6/2013 | Palmatier | A61F 2/447 623/17.16 |
| 2013/0268075 A1* | 10/2013 | McKay | A61F 2/447 623/17.16 |
| 2014/0172106 A1* | 6/2014 | To | A61F 2/442 623/17.16 |
| 2015/0100126 A1* | 4/2015 | Melkent | A61F 2/4455 623/17.16 |
| 2015/0306279 A1* | 10/2015 | El-Hibri | C08K 3/38 523/115 |
| 2019/0328540 A1* | 10/2019 | Seifert | A61F 2/4425 |

* cited by examiner

POLYMERIC SPINAL FUSION SYSTEM INCLUDING SPINAL CAGE

CROSS REFERENCE TO RELATED APPLICATION

This application is the National Stage of International Application No. PCT/US2016/033311 filed May 19, 2016, which claims the benefit of U.S. Provisional Application No. 62/163,956, filed May 19, 2015, the disclosures of which are incorporated herein by this reference in their entireties.

TECHNICAL FIELD

The disclosure generally relates to implantable medical devices and surgical instruments having improved properties, and more particularly to a spinal fusion system, including a spinal cage having improved mechanical strength and biocompatibility while promoting fusion between vertebrae.

BACKGROUND intervertebral disc degeneration is a common problem increasingly suffered by many people. Typically, this spinal problem has been addressed by removing the damaged or defective disc material and replacing it with a spinal implant which fuses two adjacent vertebrae.

Spinal fusion techniques, such as interbody fusion, involve placing a bone graft between the vertebrae in the area occupied by the intervertebral disc. The damaged disc is removed entirely in preparation for the spinal fusion. A spinal cage is then placed between the vertebrae to maintain spine alignment and disc height. Spinal fusion then takes place between the end plates of the vertebrae. Spinal fusion systems consist of a spinal cage positioned between two adjacent vertebrae to facilitate spinal fusion. The spinal fusion system also includes a rod or a plate that is connected to two adjacent vertebrae, to obtain fixation of the vertebrae with respect to each other, and can consist of a combination of both a spinal fusion cage and a rod or a plate. Insertion tools and other surgical instruments specially designed for the spinal fusion system are used to secure the spinal cage to the vertebrae.

In view of the structural integrity requirements of these implantable medical devices, the materials of fabrication are limited, and conventionally include various metal, plastic and composites. Spinal fusion systems are usually composed of metals, such as titanium or cobalt chrome alloys, or from polyetheretherketone (PEEK), a polymer that is commonly used in implantable medical devices. These implant materials, however, do not possess sufficient mechanical strength and biocompatibility for spinal fusion while also promoting fusion between the two vertebrae. Additionally, there is often mechanical incompatibility between natural bone and the implant material.

Another problem associated with implantable medical devices is infection, which may in some cases lead to sepsis and death. As a result, it is critical that implantable medical devices and the surgical instruments used to implant them are properly sterilized prior to implantation. Therefore, the devices as well as the surgical instruments must be composed of materials that are not only capable of sterilization prior to surgery, but also highly resistant to infection once they are implanted. Implantable-grade or medical-grade polymeric devices, however, are sensitive to temperature, radiation, and moisture of traditional sterilization processes.

Therefore, there is a need for an implantable medical devices that have biocompatibility, strength, flexibility, wear resistance, and radiolucency yet do not undergo meaningful loss of structural integrity, are not discolored, and do not lose electrical properties as a result of multiple sterilizations.

There is also a need for a polymeric implantable medical that is capable of being sterilized by radiation, such as gamma and E-beam sterilization procedures. Gamma and E-beam sterilization typically subjects devices to irradiation sterilization but traditional polymeric devices, in particular, will inevitably be affected by the radiation and will experience changes in their polymer structure (such as chain scission and cross-linking). These processes may lead to significant changes and compromise in the tensile strength, elongation at break, and yield strain of such polymeric devices. Furthermore, the exact changes in mechanical properties may not be immediately apparent as there can be some time delay in the development of these changes.

There is a further need for a polymeric implantable medical that is MM (magnetic resonance imaging) compatible.

Accordingly, the present disclosure provides such implantable medical devices, including spinal fusion systems and spinal cages, and surgical instruments that have improved properties over currently existing implantable medical devices and surgical instruments.

SUMMARY

In accordance with one aspect of the disclosure, a spinal fusion system including a spinal cage is disclosed. In accordance with another aspect of the disclosure, a spinal cage for implantation between two adjacent vertebrae is disclosed. The spinal cage is formed from a polymer composition comprising a polyetherimide.

BRIEF DESCRIPTION OF THE DRAWINGS

The embodiments are illustrated by way of example and are not limitation in the Figures of the accompanying drawings in which like references indicate similar elements.

DETAILED DESCRIPTION

Figure 1:
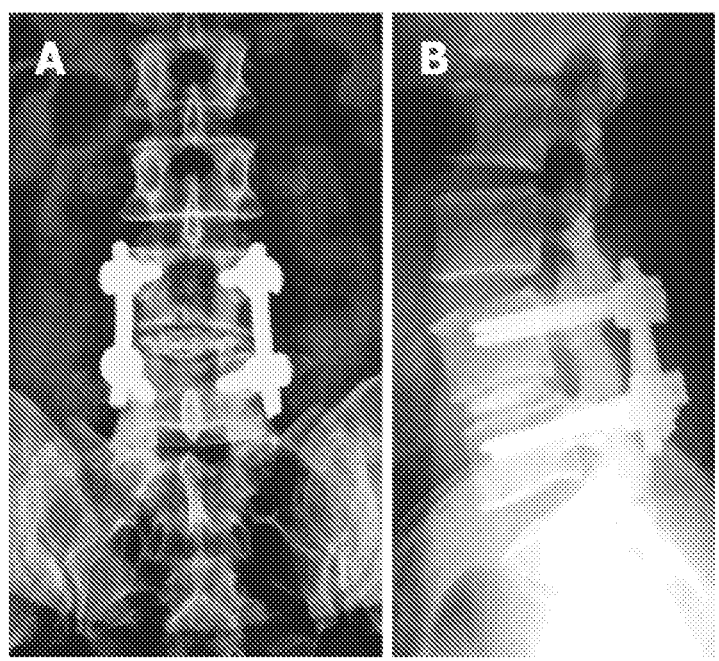
FIG. 1 shows a human spine in which an exemplary embodiment of a spinal cage may be used.
Figure 2:
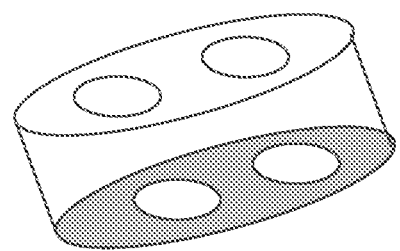
FIG. 2 shows a perspective view of an exemplary embodiment of a spinal cage that may be used.

Before the present methods and devices are disclosed and described, it is to be understood that the methods and devices are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and devices may be understood more readily by reference to the following detailed description of preferred embodiments and the Examples included therein and to the Figures and their previous and following description.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

In certain aspects of the present disclosure, implantable medical devices having improved mechanical strength and biocompatibility while promoting fusion between vertebrae are disclosed.

The Spinal Cage

In accordance with one aspect of the disclosure, a spinal fusion system including a spinal cage is disclosed. The spinal fusion system may be used in a spinal fusion surgery. Various spinal fusion surgeries and techniques are contemplated by this disclosure, including but not limited to Posterior Lumbar Interbody Fusion (PLIF), Transforaminal Lumbar Interbody Fusion (TLIF), Anterior Lumbar Interbody Fusion (ALIF) and extreme lateral interbody fusion. The spinal fusion system includes a spinal cage. In one aspect, the spinal cage is provided for implantation between adjacent vertebrae in spaced relation while promoting interbody bone ingrowth and fusion.

FIG. 1 shows a human spine in which an exemplary embodiment of a spinal cage may be used. The spine includes multiple vertebrae with intervertebral spaces containing discs of the spine. The discs may become ruptured by injury or weakened by disease or degeneration, as illustrated by the defects shown in the top disc.

As a surgical treatment, a spinal cage may be inserted within the affected intervertebral space for the purpose of fusing two or more vertebrae together. Spinal fusion may be used where one or more spinal discs have degenerated or ruptured recurrently. As is common practice, spinal cages may be inserted into the spine through various procedures commonly known as ALIF, PLIF, and TLIF procedures. To accomplish the goal of fusing certain vertebrae of the spine, the spinal cages described herein may be installed with bone cement, a demineralized bone matrix, and/or other bone growth agents in order to facilitate fusion of the vertebrae. Although these bone growth agents may be included in many of the described techniques and may be used with the described spinal cages, the details of this use of bone growth agents is not described herein in order to focus on the inventive aspects of the spinal cage that are the subject of this disclosure.

The spinal cage may include a body that approximates the shape and size of the annulus portion of a disk which normally separates two vertebral bodies. In one aspect of the disclosure, the spinal cage may have a generally rectangular body. The rectangular body may be tapered. In one aspect of the disclosure, the rectangular body may have curved surfaces to anatomically match the curvature of the vertebrae. The rectangular body may also include ridges that further serve to hold the spinal cage in place. The ridges may also reduce the possibility of the spinal cage sliding in any direction along the end plates and to prevent rotation of the spinal cage.

In one aspect, the spinal cage may include an insertion tool guide and engagement features, such as bores and notches. In one aspect, the spinal cage may include windows that allow the bone to grow from one vertebra through the cage and into the adjacent vertebra. In some embodiments, the windows may be partially or completely filled with a bone graft and/or synthetic bone material for stimulating bone growth between the adjacent vertebra.

In one aspect, the spinal fusion system includes a plate that is mated to the spinal cage. The plate is configured to receive, retain and orient bone screws, thereby holding the spinal cage and adjacent vertebrae in a stable relationship to promote fusion.

Polymer Composition

In one aspect of the disclosure, the spinal cage may be formed using a polymer composition. In one aspect of the present disclosure, the polymer composition comprises a thermoplastic resin. Other components, however, may also be included in the thermoplastic resin. For example, the polymer composition may also include a ceramic and a metal. In one aspect of the disclosure, the polymer composition used to form the spinal cage is MRI (magnetic resonance imaging) compatible.

In one aspect of the disclosure, the polymer composition is suitable for melt processing such that the spinal cage may be formed using a melt process and in particular, injection molding.

The polymer composition may include any polymeric material known in the art. The polymer composition may be composed of more than one polymeric material.

In one aspect of the disclosure, the polymers used in the polymer composition may be selected from a wide variety of thermoplastic polymers, and blends of thermoplastic polymers. The polymer composition can comprise a homopolymer, a copolymer such as a star block copolymer, a graft copolymer, an alternating block copolymer or a random copolymer, ionomer, dendrimer, or a combination comprising at least one of the foregoing. The polymer composition may also be a blend of polymers, copolymers, terpolymers, or the like, or a combination comprising at least one of the foregoing.

Examples of thermoplastic polymers that can be used in the polymer composition include polyacetals, polyacrylics, polycarbonates, polyalkyds, polystyrenes, polyolefins, polyesters, polyamides, polyaramides, polyamideimides, polyarylates, polyurethanes, epoxies, phenolics, silicones, polyarylsulfones, polyethersulfones, polyphenylene sulfides, polysulfones, polyimides, polyetherimides, polytetrafluoroethylenes, polyetherketones, polyether etherketones, polyether ketone ketones, polybenzoxazoles, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polycarboranes, polyoxabicyclononanes, polydibenzofurans, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polypropylenes, polyethylenes, polyethylene terephthalates, polyvinylidene fluorides, polysiloxanes, or the like, or a combination comprising at least one of the foregoing thermoplastic polymers.

Examples of blends of thermoplastic polymers that can be used polymer composition resin include acrylonitrile-butadiene-styrene/nylon, polycarbonate/acrylonitrile-butadiene-styrene, polyphenylene ether/polystyrene, polyphenylene ether/polyamide, polycarbonate/polyester, polyphenylene ether/polyolefin, or the like, or a combination comprising at least one of the foregoing.

In one aspect of the present disclosure, polymer composition may include, polycarbonates, polysulfones, polyesters, polyamides, polypropylene. In a further aspect, the polyimides used in the disclosed polymer composition may include polyamideimides, polyetherimides and polybenzimidazoles. In a further aspect, polyetherimides comprise melt processable polyetherimides.

Polyetherimides

In one aspect of the disclosure, the polymer composition includes a polyetherimide. In an aspect, polyetherimides can comprise polyetherimides homopolymers (e.g., polyetherimidesulfones) and polyetherimides copolymers. The polyetherimide can be selected from (i) polyetherimidehomopolymers, e.g., polyetherimides, (ii) polyetherimide copolymers, and (iii) combinations thereof. Polyetherimides are known polymers and are sold by SABIC Innovative Plastics under the ULTEM®*, EXTEM®*, and Siltem* brands (Trademark of SABIC Innovative Plastics IP B.V.).

In an aspect, the polyetherimides can be of formula (1):

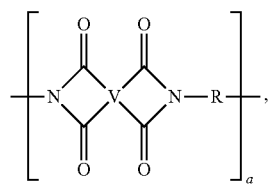

wherein a is more than 1, for example 10 to 1,000 or more, or more specifically 10 to 500.

The group V in formula (1) is a tetravalent linker containing an ether group (a "polyetherimide" as used herein) or a combination of an ether groups and arylenesulfone groups (a "polyetherimidesulfone"). Such linkers include but are not limited to: (a) substituted or unsubstituted, saturated, unsaturated or aromatic monocyclic and polycyclic groups having 5 to 50 carbon atoms, optionally substituted with ether groups, arylenesulfone groups, or a combination of ether groups and arylenesulfone groups; and (b) substituted or unsubstituted, linear or branched, saturated or unsaturated alkyl groups having 1 to 30 carbon atoms and optionally substituted with ether groups or a combination of ether groups, arylenesulfone groups, and arylenesulfone groups; or combinations comprising at least one of the foregoing. Suitable additional substitutions include, but are not limited to, ethers, amides, esters, and combinations comprising at least one of the foregoing.

The R group in formula (1) includes but is not limited to substituted or unsubstituted divalent organic groups such as: (a) aromatic hydrocarbon groups having 6 to 20 carbon atoms and halogenated derivatives thereof, (b) straight or branched chain alkylene groups having 2 to 20 carbon atoms; (c) cycloalkylene groups having 3 to 20 carbon atoms, or (d) divalent groups of formula (2):

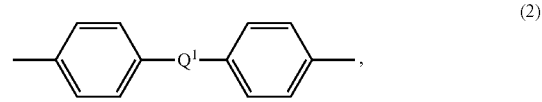

wherein Q1 includes but is not limited to a divalent moiety such as —O—, —S—, —C(O)—, —SO2-, —SO—, —CyH2y- (y being an integer from 1 to 5), and halogenated derivatives thereof, including perfluoroalkylene groups.

In an embodiment, linkers V include but are not limited to tetravalent aromatic groups of formula (3):

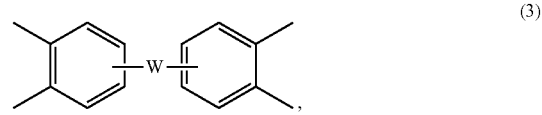

wherein W is a divalent moiety including —O—, —SO2-, or a group of the formula —O—Z—O— wherein the divalent bonds of the —O— or the —O—Z—O— group are in the 3,3', 3,4', 4,3', or the 4,4' positions, and wherein Z includes, but is not limited, to divalent groups of formulas (4):

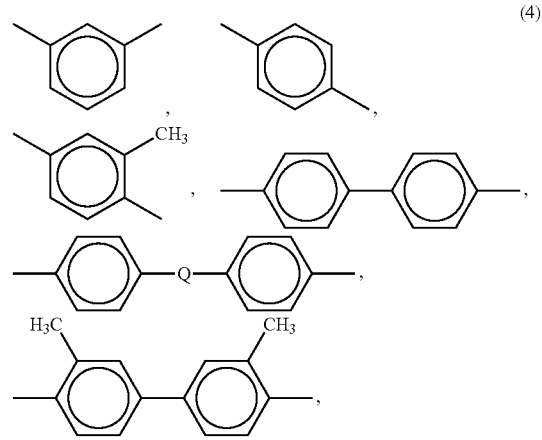

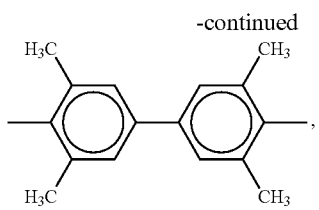

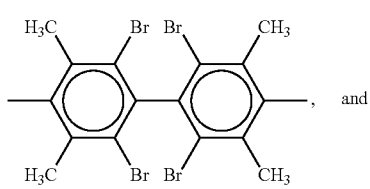
and

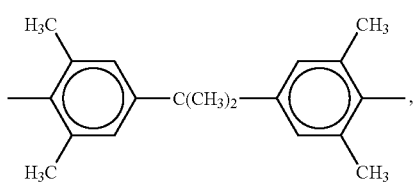

wherein Q includes, but is not limited to a divalent moiety including —O—, —S—, —C(O), —SO$_2$—, —SO—, —C$_y$H$_{2y}$— (y being an integer from 1 to 5), and halogenated derivatives thereof, including perfluoroalkylene groups.

In an aspect, the polyetherimide comprise more than 1, specifically 10 to 1,000, or more specifically, 10 to 500 structural units, of formula (5):

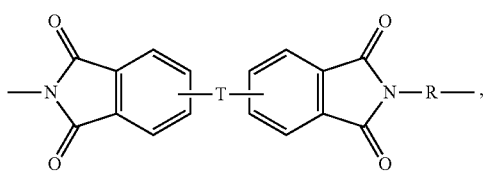
(5)

wherein T is —O— or a group of the formula —O—Z—O— wherein the divalent bonds of the —O— or the —O—Z—O— group are in the 3,3', 3,4', 4,3', or the 4,4' positions; Z is a divalent group of formula (3) as defined above; and R is a divalent group of formula (2) as defined above.

In another aspect, the polyetherimidesulfones are polyetherimides comprising ether groups and sulfone groups wherein at least 50 mole % of the linkers V and the groups R in formula (1) comprise a divalent arylenesulfone group. For example, all linkers V, but no groups R, can contain an arylenesulfone group; or all groups R but no linkers V can contain an arylenesulfone group; or an arylenesulfone can be present in some fraction of the linkers V and R groups, provided that the total mole fraction of V and R groups containing an aryl sulfone group is greater than or equal to 50 mole %.

Even more specifically, polyetherimidesulfones can comprise more than 1, specifically 10 to 1,000, or more specifically, 10 to 500 structural units of formula (6):

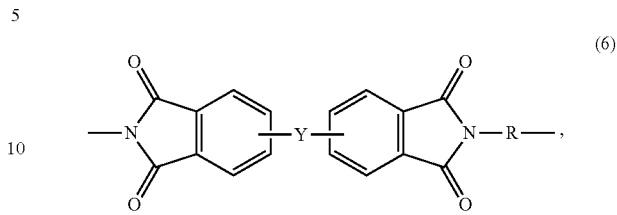
(6)

wherein Y is —O—, —SO2-, or a group of the formula —O—Z—O— wherein the divalent bonds of the —O—, SO2-, or the —O—Z—O— group are in the 3,3', 3,4', 4,3', or the 4,4' positions, wherein Z is a divalent group of formula (3) as defined above and R is a divalent group of formula (2) as defined above, provided that greater than 50 mole % of the sum of moles Y+moles R in formula (2) contain —SO2- groups.

It is to be understood that the polyetherimides and polyetherimidesulfones can optionally comprise linkers V that do not contain ether or ether and sulfone groups, for example linkers of formula (7):

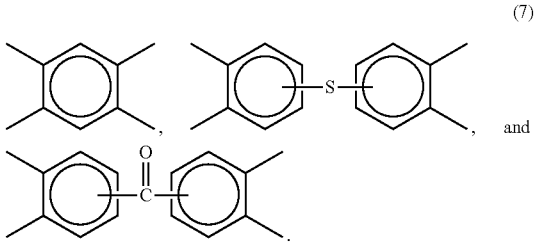
(7)

Imide units containing such linkers are generally be present in amounts ranging from 0 to 10 mole % of the total number of units, specifically 0 to 5 mole %. In one embodiment no additional linkers V are present in the polyetherimides and polyetherimidesulfones.

In another aspect, the polyetherimide comprises 10 to 500 structural units of formula (5) and the polyetherimidesulfone contains 10 to 500 structural units of formula (6).

Polyetherimides and polyetherimidesulfones can be prepared by any suitable process. In one embodiment, polyetherimides and polyetherimide copolymers include polycondensation polymerization processes and halo-displacement polymerization processes.

Polycondensation methods can include a method for the preparation of polyetherimides having structure (1) is referred to as the nitro-displacement process (X is nitro in formula (8)). In one example of the nitro-displacement process, N-methyl phthalimide is nitrated with 99% nitric acid to yield a mixture of N-methyl-4-nitrophthalimide (4-NPI) and N-methyl-3-nitrophthalimide (3-NPI). After purification, the mixture, containing approximately 95 parts of 4-NPI and 5 parts of 3-NPI, is reacted in toluene with the disodium salt of bisphenol-A (BPA) in the presence of a phase transfer catalyst. This reaction yields BPA-bisimide and NaNO2 in what is known as the nitro-displacement step. After purification, the BPA-bisimide is reacted with phthalic anhydride in an imide exchange reaction to afford BPA-dianhydride (BPADA), which in turn is reacted with a diamine such as meta-phenylene diamine (MPD) in ortho-dichlorobenzene in an imidization-polymerization step to afford the product polyetherimide.

Other diamines are also possible. Examples of suitable diamines include: m-phenylenediamine; p-phenylenediamine; 2,4-diaminotoluene; 2,6-diaminotoluene; m-xylylenediamine; p-xylylenediamine; benzidine; 3,3'-dimethylbenzidine; 3,3'-dimethoxybenzidine; 1,5-diaminonaphthalene; bis(4-aminophenyl)methane; bis(4-aminophenyl)propane; bis(4-aminophenyl)sulfide; bis(4-aminophenyl)sulfone; bis(4-aminophenyl)ether; 4,4'-diaminodiphenylpropane; 4,4'-diaminodiphenylmethane(4,4'-methylenedianiline); 4,4'-diaminodiphenylsulfide; 4,4'-diaminodiphenylsulfone; 4,4'-diaminodiphenylether(4,4'-oxydianiline); 1,5-diaminonaphthalene; 3,3'dimethylbenzidine; 3-methylheptamethylenediamine; 4,4-dimethylheptamethylenediamine; 2,2',3,3'-tetrahydro-3,3,3',3'-tetramethyl-1,1'-spirobi[1H-indene]-6,6'-diamine; 3,3',4,4'-tetrahydro-4,4,4',4'-tetramethyl-2,2'-spirobi[2H-1-benzo-pyran]-7,7'-diamine; 1,1'-bis[1-amino-2-methyl-4-phenyl]cyclohexane, and isomers thereof as well as mixtures and blends comprising at least one of the foregoing. In one embodiment, the diamines are specifically aromatic diamines, especially m- and p-phenylenediamine and mixtures comprising at least one of the foregoing.

Suitable dianhydrides that can be used with the diamines include and are not limited to 2,2-bis[4-(3,4-dicarboxyphenoxy)phenyl]propane dianhydride; 4,4'-bis(3,4-dicarboxyphenoxy)diphenyletherdianhydride; 4,4'-bis(3,4-dicarboxyphenoxy)diphenylsulfidedianhydride; 4,4'-bis(3,4-dicarboxyphenoxy)benzophenonedianhydride; 4,4'-bis(3,4-dicarboxyphenoxy)diphenylsulfonedianhydride; 2,2-bis[4-(2,3-dicarboxyphenoxy)phenyl]propane dianhydride; 4,4'-bis(2,3-dicarboxyphenoxy)diphenyletherdianhydride; 4,4'-bis(2,3-dicarboxyphenoxy)diphenylsulfidedianhydride; 4,4'-bis(2,3-dicarboxyphenoxy)benzophenonedianhydride; 4,4'-bis(2,3-dicarboxyphenoxy)diphenylsulfonedianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy) diphenyletherdianhydride; 4-(2,3-dicarboxyphenoxy)-4'-(3,4-dicarboxyphenoxy)diphenylsulfide dianhydride; 4-(2,3-dicarboxyphenoxy)-4'-(3,4-dicarboxyphenoxy) benzophenonedianhydride; 4-(2,3-dicarboxyphenoxy)-4'-(3,4-dicarboxyphenoxy)diphenylsulfone dianhydride; 1,3-bis (2,3-dicarboxyphenoxy)benzene dianhydride; 1,4-bis(2,3-dicarboxyphenoxy)benzene dianhydride; 1,3-bis(3,4-dicarboxyphenoxy)benzene dianhydride; 1,4-bis(3,4-dicarboxyphenoxy)benzene dianhydride; 3,3',4,4'-diphenyl tetracarboxylicdianhydride; 3,3',4,4'-benzophenonetetracarboxylic dianhydride; naphthalicdianhydrides, such as 2,3,6,7-naphthalic dianhydride, etc.; 3,3',4,4'-biphenylsulphonictetracarboxylic dianhydride; 3,3',4,4'-biphenylethertetracarboxylic dianhydride; 3,3',4,4'-dimethyldiphenylsilanetetracarboxylic dianhydride; 4,4'-bis (3,4-dicarboxyphenoxy)diphenylsulfidedianhydride; 4,4'-bis (3,4-dicarboxyphenoxy)diphenylsulphonedianhydride; 4,4'-bis (3,4-dicarboxyphenoxy)diphenylpropanedianhydride; 3,3',4,4'-biphenyltetracarboxylic dianhydride; bis(phthalic)phenylsulphineoxidedianhydride; p-phenylene-bis(triphenylphthalic)dianhydride; m-phenylene-bis(triphenylphthalic)dianhydride; bis(triphenylphthalic)-4,4'-diphenylether dianhydride; bis(triphenylphthalic)-4,4'-diphenylmethane dianhydride; 2,2'-bis(3,4-dicarboxyphenyl)hexafluoropropanedianhydride; 4,4'-oxydiphthalic dianhydride; pyromelliticdianhydride; 3,3',4, 4'-diphenylsulfonetetracarboxylic dianhydride; 4',4'-bisphenol A dianhydride; hydroquinone diphthalic dianhydride; 6,6'-bis(3,4-dicarboxyphenoxy)-2,2',3,3'-tetrahydro-3,3,3',3'-tetramethyl-1,1'-spirobi[1H-indene]dianhydride; 7,7'-bis (3,4-dicarboxyphenoxy)-3,3',4,4'-tetrahydro-4,4,4',4'-tetramethyl-2,2'-spirobi[2H-1-benzopyran]dianhydride; 1,1'-bis[1-(3,4-dicarboxyphenoxy)-2-methyl-4-phenyl] cyclohexane dianhydride; 3,3',4,4'-diphenylsulfonetetracarboxylic dianhydride; 3,3',4,4'-diphenylsulfidetetracarboxylic dianhydride; 3,3',4,4'-diphenylsulfoxidetetracarboxylic dianhydride; 4,4'-oxydiphthalic dianhydride; 3,4'-oxydiphthalic dianhydride; 3,3'-oxydiphthalic dianhydride; 3,3'-benzophenonetetracarboxylic dianhydride; 4,4'-carbonyldiphthalic dianhydride; 3,3',4,4'-diphenylmethanetetracarboxylic dianhydride; 2,2-bis(4-(3,3-dicarboxyphenyl)propane dianhydride; 2,2-bis(4-(3,3-dicarboxyphenyl)hexafluoropropanedianhydride; (3,3', 4,4'-diphenyl)phenylphosphinetetracarboxylicdianhydride; (3,3',4,4'-diphenyl)phenylphosphineoxidetetracarboxylicdianhydride; 2,2'-dichloro-3,3',4,4'-biphenyltetracarboxylic dianhydride; 2,2'-dimethyl-3,3',4,4'-biphenyltetracarboxylic dianhydride; 2,2'-dicyano-3,3',4,4'-biphenyltetracarboxylic dianhydride; 2,2'-dibromo-3,3',4,4'-biphenyltetracarboxylic dianhydride; 2,2'-diiodo-3,3',4,4'-biphenyltetracarboxylic dianhydride; 2,2'-ditrifluoromethyl-3,3',4,4'-biphenyltetracarboxylic dianhydride; 2,2'-bis(1-methyl-4-phenyl)-3,3',4,4'-biphenyltetracarboxylic dianhydride; 2,2'-bis(1-trifluoromethyl-2-phenyl)-3,3',4,4'-biphenyltetracarboxylic dianhydride; 2,2'-bis(1-trifluoromethyl-3-phenyl)-3,3',4,4'-biphenyltetracarboxylic dianhydride; 2,2'-bis(1-trifluoromethyl-4-phenyl)-3,3',4,4'-biphenyltetracarboxylic dianhydride; 2,2'-bis(1-phenyl-4-phenyl)-3,3',4,4'-biphenyltetracarboxylic dianhydride; 4,4'-bisphenol A dianhydride; 3,4'-bisphenol A dianhydride; 3,3'-bisphenol A dianhydride; 3,3',4,4'-diphenylsulfoxidetetracarboxylic dianhydride; 4,4'-carbonyldiphthalic dianhydride; 3,3',4,4'-diphenylmethanetetracarboxylic dianhydride; 2,2'-bis(1,3-trifluoromethyl-4-phenyl)-3,3',4,4'-biphenyltetracarboxylic dianhydride, and all isomers thereof, as well as combinations of the foregoing.

Halo-displacement polymerization methods for making polyetherimides and polyetherimidesulfones include and are not limited to, the reaction of a bis(phthalimide) for formula (8):

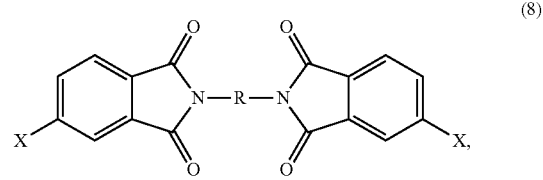

(8)

wherein R is as described above and X is a nitro group or a halogen. Bis-phthalimides (8) can be formed, for example, by the condensation of the corresponding anhydride of formula (9):

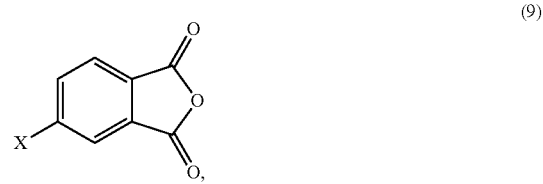

(9)

wherein X is a nitro group or halogen, with an organic diamine of the formula (10):

$$H_2N—R—NH_2 \quad (10),$$

wherein R is as described above.

Illustrative examples of amine compounds of formula (10) include: ethylenediamine, propylenediamine, trimethylenediamine, diethylenetriamine, triethylenetetramine, hexamethylenediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis (3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(b-amino-t-butyl) toluene, bis(p-b-amino-t-butylphenyl) ether, bis(p-b-methyl-o-aminophenyl) benzene, bis(p-b-methyl-o-aminopentyl) benzene, 1,3-diamino-4-isopropylbenzene, bis(4-aminophenyl) ether and 1,3-bis(3-aminopropyl) tetramethyldisiloxane. Mixtures of these amines can be used. Illustrative examples of amine compounds of formula (10) containing sulfone groups include but are not limited to, diaminodiphenylsulfone (DDS) and bis(aminophenoxy phenyl) sulfones (BAPS). Combinations comprising any of the foregoing amines can be used.

The polyetherimides can be synthesized by the reaction of the bis(phthalimide) (8) with an alkali metal salt of a dihydroxy substituted aromatic hydrocarbon of the formula HO—V—OH wherein V is as described above, in the presence or absence of phase transfer catalyst. Suitable phase transfer catalysts are disclosed in U.S. Pat. No. 5,229,482. Specifically, the dihydroxy substituted aromatic hydrocarbon a bisphenol such as bisphenol A, or a combination of an alkali metal salt of a bisphenol and an alkali metal salt of another dihydroxy substituted aromatic hydrocarbon can be used.

In one embodiment, the polyetherimide comprises structural units of formula (5) wherein each R is independently p-phenylene or m-phenylene or a mixture comprising at least one of the foregoing; and T is group of the formula —O—Z—O— wherein the divalent bonds of the —O—Z—O— group are in the 3,3' positions, and Z is 2,2-diphenylenepropane group (a bisphenol A group). Further, the polyetherimidesulfone comprises structural units of formula (6) wherein at least 50 mole % of the R groups are of formula (4) wherein Q is —SO2- and the remaining R groups are independently p-phenylene or m-phenylene or a combination comprising at least one of the foregoing; and T is group of the formula —O—Z—O— wherein the divalent bonds of the —O—Z—O— group are in the 3,3' positions, and Z is a 2,2-diphenylenepropane group.

The polyetherimide and polyetherimidesulfone can be used alone or in combination with each other and/or other of the disclosed polymeric materials in fabricating the polymeric components of the invention. In one embodiment, only the polyetherimide is used. In another embodiment, the weight ratio of polyetherimide:polyetherimidesulfone can be from 99:1 to 50:50.

The polyetherimides can have a weight average molecular weight (Mw) of 5,000 to 100,000 grams per mole (g/mole) as measured by gel permeation chromatography (GPC). In some embodiments the Mw can be 10,000 to 80,000. The molecular weights as used herein refer to the absolute weight averaged molecular weight (Mw).

The polyetherimides can have an intrinsic viscosity greater than or equal to 0.2 deciliters per gram (dl/g) as measured in m-cresol at 25° C. Within this range the intrinsic viscosity can be 0.35 to 1.0 dl/g, as measured in m-cresol at 25° C.

The polyetherimides can have a glass transition temperature of greater than 180° C., specifically of 200° C. to 500° C., as measured using differential scanning calorimetry (DSC) per ASTM test D3418. In some embodiments, the polyetherimide and, in particular, a polyetherimide has a glass transition temperature of 240 to 350° C.

The polyetherimides can have a melt index of 0.1 to 10 grams per minute (g/min), as measured by American Society for Testing Materials (ASTM) DI 238 at 340 to 370° C., using a 6.7 kilogram (kg) weight.

In certain aspects, the polyetherimides of the present disclosure may be unfilled, standard flow grades (PEI-1 in Tables 1-2) or unfilled, high flow grades (PEI-2 in Tables 1-2), or may be filled, for example, with carbon (e.g., carbon fiber) or glass. Filled polymer components may include between 40 wt % and 90 wt % of the polyetherimide resin and between 10 wt % and 60 wt % of a filler by weight of the polymer component. Other formulations may be used.

An alternative halo-displacement polymerization process for making polyetherimides, e.g., polyetherimides having structure (1) is a process referred to as the chloro-displacement process (X is Cl in formula (8)). The chloro-displacement process is illustrated as follows: 4-chloro phthalic anhydride and meta-phenylene diamine are reacted in the presence of a catalytic amount of sodium phenyl phosphinate catalyst to produce the bischlorophthalimide of meta-phenylene diamine (CAS No. 148935-94-8). The bischlorophthalimide is then subjected to polymerization by chloro-displacement reaction with the disodium salt of BPA in the presence of a catalyst in ortho-dichlorobenzene or anisole solvent. Alternatively, mixtures of 3-chloro- and 4-chlorophthalic anhydride may be employed to provide a mixture of isomeric bischlorophthalimides which may be polymerized by chloro-displacement with BPA disodium salt as described above.

Siloxane polyetherimides can include polysiloxane/polyetherimide block or random copolymers having a siloxane content of greater than 0 and less than 40 weight percent (wt %) based on the total weight of the block copolymer. The block copolymer comprises a siloxane block of Formula (I):

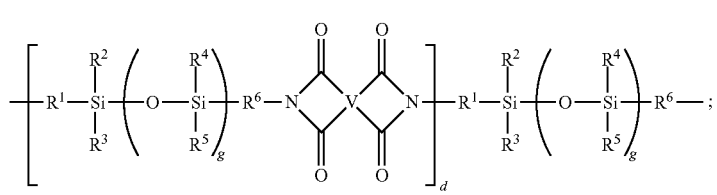

wherein $R^{1-6}$ are independently at each occurrence selected from the group consisting of substituted or unsubstituted, saturated, unsaturated, or aromatic monocyclic groups having 5 to 30 carbon atoms, substituted or unsubstituted, saturated, unsaturated, or aromatic polycyclic groups having 5 to 30 carbon atoms, substituted or unsubstituted alkyl groups having 1 to 30 carbon atoms and substituted or unsubstituted alkenyl groups having 2 to 30 carbon atoms, V is a tetravalent linker selected from the group consisting of substituted or unsubstituted, saturated, unsaturated, or aromatic monocyclic and polycyclic groups having 5 to 50 carbon atoms, substituted or unsubstituted alkyl groups having 1 to 30 carbon atoms, substituted or unsubstituted alkenyl groups having 2 to 30 carbon atoms and combinations comprising at least one of the foregoing linkers, g equals 1 to 30, and d is 2 to 20. Commercially available siloxane polyetherimides can be obtained from SABIC Innovative Plastics under the brand name SILTEM* (*Trademark of SABIC Innovative Plastics IP B.V.)

The polyetherimide resin can have a weight average molecular weight (Mw) within a range having a lower limit and/or an upper limit. The range can include or exclude the lower limit and/or the upper limit. The lower limit and/or upper limit can be selected from 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 51000, 52000, 53000, 54000, 55000, 56000, 57000, 58000, 59000, 60000, 61000, 62000, 63000, 64000, 65000, 66000, 67000, 68000, 69000, 70000, 71000, 72000, 73000, 74000, 75000, 76000, 77000, 78000, 79000, 80000, 81000, 82000, 83000, 84000, 85000, 86000, 87000, 88000, 89000, 90000, 91000, 92000, 93000, 94000, 95000, 96000, 97000, 98000, 99000, 100000, 101000, 102000, 103000, 104000, 105000, 106000, 107000, 108000, 109000, and 110000 daltons. For example, the polyetherimide resin can have a weight average molecular weight (Mw) from 5,000 to 100,000 daltons, from 5,000 to 80,000 daltons, or from 5,000 to 70,000 daltons. The primary alkyl amine modified polyetherimide will have lower molecular weight and higher melt flow than the starting, unmodified, polyetherimide.

The polyetherimide resin can be selected from the group consisting of a polyetherimide, for example as described in U.S. Pat. Nos. 3,875,116; 6,919,422 and 6,355,723 a silicone polyetherimide, for example as described in U.S. Pat. Nos. 4,690,997; 4,808,686 a polyetherimidesulfone resin, as described in U.S. Pat. No. 7,041,773 and combinations thereof, each of these patents are incorporated herein their entirety.

The polyetherimide resin can have a glass transition temperature within a range having a lower limit and/or an upper limit. The range can include or exclude the lower limit and/or the upper limit. The lower limit and/or upper limit can be selected from 100, 110, 120, 130, 140, 150, 160, 170, 180, 190, 200, 210, 220, 230, 240, 250, 260, 270, 280, 290, 300 and 310 degrees Celsius. For example, the polyetherimide resin can have a glass transition temperature (Tg) greater than about 200 degrees Celsius.

The polyetherimide resin can be substantially free (less than 100 ppm) of benzylic protons. The polyetherimide resin can be free of benzylic protons. The polyetherimide resin can have an amount of benzylic protons below 100 ppm. In one embodiment, the amount of benzylic protons ranges from more than 0 to below 100 ppm. In another embodiment, the amount of benzylic protons is not detectable.

The polyetherimide resin can be substantially free (less than 100 ppm) of halogen atoms. The polyetherimide resin can be free of halogen atoms. The polyetherimide resin can have an amount of halogen atoms below 100 ppm. In one embodiment, the amount of halogen atoms range from more than 0 to below 100 ppm. In another embodiment, the amount of halogen atoms is not detectable.

Therapeutic Agents

In certain aspects of the disclosure, the spinal fusion system may additionally include certain therapeutic agents that are commonly used to promote bone fusion or ingrowth. Such therapeutic agents may include natural or synthetic therapeutic agents such as bone morphogenic proteins (BMPs), growth factors, bone marrow aspirate, stem cells, progenitor cells, antibiotics, or other osteoconductive, osteoinductive, osteogenic, or any other fusion enhancing material or beneficial therapeutic agent.

In one aspect, the spinal cage includes a coating formed on surfaces of the cage. The coating, for example, may be a biomimetic and/or osteogenic (e.g., bone morphogenetic protein(s) (BMP) and related compounds) coating. In certain aspects, the coating may be used to enhance bone growth on the spinal cage. In some aspects, the coating may be formed on substantially all of the surfaces of the spinal cage; though, in other aspects, only a portion of the surfaces are coated; and, in some embodiments, the spinal cage may not be coated at all. Suitable coating materials include calcium phosphate, BMP and related compounds, amongst others.

In some aspects, a substance (e.g., a drug) may elute from the spinal cage and/or a coating on the spinal cage. For example, a substance incorporated into the spinal cage and/or coating may be emitted into regions around the implant cage (e.g., within the windows). In some aspects, the substance (e.g., BMP and related compounds) may be selected to enhance bone growth. The substance, for example, may be incorporated at different concentrations into different locations of the spinal cage and/or coating.

In certain aspects of the disclosure, the polymer composition may also include a biocide. The biocide may be selected from germicides, antimicrobials, antibiotics, antibacterials, antiyeasts, antialgals, antivirals, antifungals, antiprotozoals, antiparasites, and combinations thereof.

In certain aspects of the disclosure, the spinal cage and/or the rod or plate may be formed by any method or combination of methods known in the art. These methods include, but are not limited to, molding processes, additive manufacturing, and machining. These molding processes include, but are not limited to, various melt forming process, injection molding, blow molding (stretch, extrusion or injection), sheet and film extrusion, profile extrusion, thermoforming, additive manufacturing, compression molding, fiber extrusion, powder sintering, transfer molding, reaction injection (RIM) molding, vacuum forming, cold casting, dip molding, slush molding and press molding. In one aspect, a combination of these molding methods may be used to form the spinal cage and/or the plate.

Various surgical instruments may be used to secure the spinal cage to the vertebrae. For example, a screw driver, a distractor, a reamer, a ring curette, a holder, a graft pusher, an impactor, a forked impactor, and/or a final impactor may be used. A spinal cage may be secured to the vertebrae via anterior lumbar interbody fusion (ALIF) surgery or posterior lumbar interbody fusion (PLIF). In ALIF, the spinal cage is inserted into the body from the front of the body, such as from the abdomen, while in PLIF the spinal cage is inserted into the body from the back, such as from the lower back. For example, in ALIF, patients are positions on their backs and given an anesthesia. The surgeon may make an incision on one side of the abdomen and move the organs and blood vessels to one side to expose the front of the spine. The problem disc may be located using several means, one of which is a fluoroscope. After the problem disc has been located, the surgeon may drill two holes through the front of the disc. The spinal cage is designed to fit into the drilled holes. The spinal cage may be fitted to the drilled holes using the distractor, the reamer, the ring curette, the holder, and/or the various types of impactors. These instruments may be used on a standalone basis or multiple instruments may be used in conjunction. Bone graft material may be packed into the hollow spinal cage. Bone graft material may be bone graft from another part of the body, such as the pelvis, or it may be a bone graft substitute. The graft pusher may be used to pack the graft material into the hollow spinal cage. The surgeon may then use the screwdriver to screw the spinal cage into the holes. The threads of the spinal cage clinch the vertebrae above and below. Alternatively, instead of inserting the spinal cage into the body using one incision, multiple, smaller incisions may be used. PLIF is analogous to ALIF except that the spinal cage is inserted from the back.

In certain aspects of the disclosure, the surgical instruments may also be formed using the polymer composition disclosed herein. The implantable medical device of this or any other aspect of the disclosure may be any implant or instrument used to accomplish a medical procedure. The medical device of some aspects of the disclosure is capable of undergoing one or more sterilizations, without degrading in a manner that would make the device unsuitable for use in a medical procedure. The sterilizations may be from steam autoclave sterilization cycles or from application of a chemical sterilizing substance, or from any other effective sterilization substance or process, including, dry heat, ethylene oxide gas, vaporized hydrogen peroxide, or other sterilization procedures.

Aspects

The present disclosure comprises at least the following aspects.

Aspect 1. A spinal cage for implantation between two adjacent vertebrae, wherein the spinal cage comprises a polymer composition, the polymer composition comprising a polyetherimide.

Aspect 2. The spinal cage of aspect 1, wherein the polyetherimide comprises structural units derived from at least one diamine selected from 1,3-diaminobenzene, 1,4-diaminobenzene, 4,4'-diaminodiphenyl sulfone, oxydianiline, 1,3-bis(4-aminophenoxy)benzene, or combinations thereof.

Aspect 3. The spinal cage of any preceding aspect, wherein the polyetherimide has a weight average molecular weight of at least about 10,000 to about 150.00 grams per mole (g/mol).

Aspect 4. The spinal cage of any preceding aspect, wherein the polyetherimide has less than 100 ppm amine end groups.

Aspect 5. The spinal cage of any preceding aspect, further comprising a biocide, wherein the biocide is selected from germicides, antimicrobials, antibiotics, antibacterials, antiyeasts, antialgals, antivirals, antifungals, antiprotozoals, antiparasites, and combinations thereof.

Aspect 6. The medical device of any preceding aspect, wherein the header is formed from a polymer component comprising between 40 wt % and 90 wt % of the polyetherimide resin and between 10 wt % and 60 wt % of a filler by weight of the polymer component.

Aspect 7. The medical device of aspect 6, wherein the filler comprises glass, carbon, carbon fiber, or a combination thereof.

Aspect 8. The spinal cage of any preceding aspect, wherein the polymer composition further comprises ceramic or metal.

Aspect 9. The spinal cage of any preceding aspect, wherein polyetherimide comprises repeating units of the formula

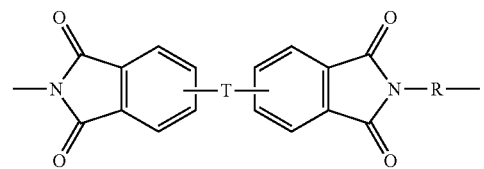

wherein R is a divalent radical of the formula

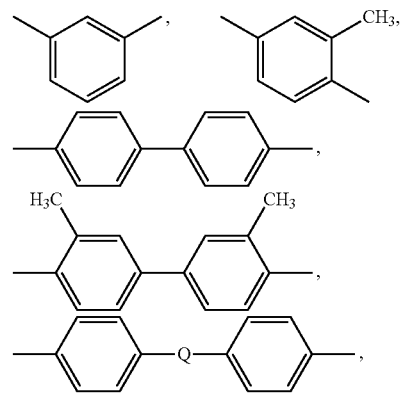

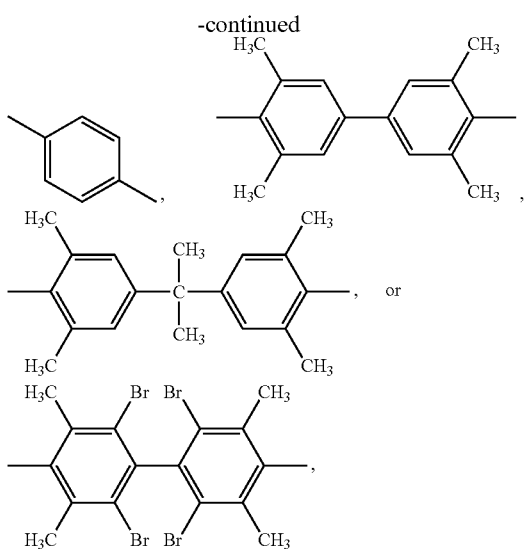

or combinations thereof wherein Q is selected from —O—, —S—, —C(O)—, —SO$_2$—, —SO—, and —C$_y$H$_{2y}$— wherein y is an integer from 1 to 5; and T is —O— or a group of the formula —O—Z—O— wherein the divalent bonds of the —O— or the —O—Z—O— group are in the 3,3', 3,4', 4,3', or the 4,4' positions and Z is a divalent group of the formula

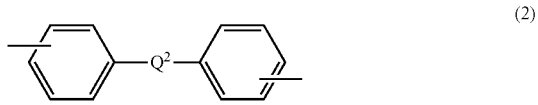
(2)

wherein Q$^2$ is selected from —O—, —S—, —C(O)—, —SO$_2$—, —SO—, and —C$_y$H$_{2y}$— wherein y is an integer from 1 to 5.

Aspect 10. The spinal cage according to any of the preceding aspects, wherein the spinal cage is sterilized using at least one sterilization process selected from the group consisting of: steam autoclave sterilization, hydrogen peroxide sterilization, gamma-ray sterilization and ethylene oxide sterilization.

Aspect 11. The spinal cage according to any of the preceding aspects, wherein the spinal cage has a compressive strength after sterilization that is within 5% of the compressive strength of the spinal cage prior to sterilization.

Aspect 12. A spinal fusion system comprising: the spinal cage according to any of the preceding aspects and a plate, wherein the plate secures the spinal cage to the vertebrae.

Aspect 13. The spinal fusion system of aspect 10, wherein the plate comprises polyetherimide.

Aspect 14. A method of treating a spine of a patient comprising: removing a damaged spinal disk and inserting the spinal cage according to any of the previous aspects into an area of the spine that contained the damaged spinal disk, wherein the spinal cage is formed from a polyetherimide comprising structural units derived from at least one diamine selected from 1,3-diaminobenzene, 1,4-diaminobenzene, 4,4'-diaminodiphenyl sulfone, oxydianiline, 1,3-bis(4-aminophenoxy)benzene, or combinations thereof.

Aspect 15. The method of aspect 14, wherein the polyetherimide has a weight average molecular weight of at least about 10,000 to about 150.00 grams per mole (g/mol).

Aspect 16. The method of any one of aspects 14-15, wherein the polyetherimide has less than 100 ppm amine end groups.

Aspect 17. The method of any one of aspects 14-16, further comprising a biocide, wherein the biocide is selected from germicides, antimicrobials, antibiotics, antibacterials, antiyeasts, antialgals, antivirals, antifungals, antiprotozoals, antiparasites, and combinations thereof.

Aspect 18. The method of any one of aspects 14-17, wherein the spinal cage is formed from a polymer component comprising between 40 wt % and 90 wt % of the polyetherimide and between 10 wt % and 60 wt % of a filler by weight of the polymer component.

Aspect 19. The method of aspect 18, wherein the filler comprises glass, carbon, carbon fiber, or a combination thereof.

Aspect 20. The method of any one of aspects 14-19, wherein the polymer composition further comprises ceramic or metal.

As an illustrative example, the polyetherimides used in forming the apparatus of the present disclosure may exhibit distinguishable properties over other comparative polymers, as shown in Tables 1-2 (PEI—polyetherimide; PPSU—polyphenylsulfone; PSU—polysulfone; PEEK—Polyether ether ketone; TPU—thermoplastic polyurethane):

TABLE 1

| Polymer Type | | | E1 | E2 | CE1 | CE2 | CE3 |
|---|---|---|---|---|---|---|---|
| MECHANICAL | Unit | Standard | PEI-1 | PEI-2 | PPSU | PSU | PEEK |
| Tensile Stress @ Yield, Type I, 5 mm/min | kgf/cm$^2$ | ASTM D 638 | 1120 | 1120 | 710 | 720 | 1020 |
| Tensile Modulus, 5 mm/min | kgf/cm$^2$ | ASTM D 638 | 36500 | 36500 | 23900 | 25300 | 37700 |
| Flexural Stress @ Yield, 1.3 mm/min, 50 mm span | kgf/cm$^2$ | ASTM D 790 | 1760 | 1770 | 930 | 1080 | 1560 |
| Flexural Modulus, 1.3 mm/min, 50 mm span | kgf/cm$^2$ | ASTM D 790 | 35000 | 34900 | 24600 | 27400 | 38700 |
| IMPACT | Unit | Standard | Value | | | | |
| Izod Impact, notched, 23° C. | cm-kgf/cm | ASTM D 256 | 5 | 3 | 70 | 7.0 | 5.4 |

TABLE 1-continued

| PHYSICAL | Unit | Standard | Value | | | | |
|---|---|---|---|---|---|---|---|
| Specific Gravity | — | ASTM D 792 | 1.27 | 1.27 | 1.29 | 1.24 | 1.30 |
| Melt Flow Rate, 400° C./2.16 kgf | g/10 min | ASTM D 1238 | — | — | — | — | 36 |
| Melt Flow Rate, 365° C./5.0 kgf | g/10 min | ASTM D 1238 | — | — | 14-20 | — | — |
| Melt Flow Rate, 343° C./2.16 kgf | g/10 min | ASTM D 1238 | — | — | — | 6.5 | — |
| Melt Flow Rate, 337° C./6.6 kgf | g/10 min | ASTM D 1238 | 9 | 17.8 | — | — | — |
| ELECTRICAL | Unit | Standard | Value | | | | |
| Volume Resistivity | Ohm-cm | ASTM D 257 | 1.00E+17 | 1.00E+17 | 9.00E+15 | 3.00E+16 | — |
| THERMAL | Unit | Standard | Value | | | | |
| Glass Transition Temperature | ° C. | | 217 | 217 | 220 | — | 147 |
| Heat Deflection Temperature, 1.82 MPa | ° C. | ASTM D 648 | 201 | 198 | 207 | 174 | 160 |

TABLE 2

| Polymer Type | | | E1 | E2 | CE4 | CE5 | CE6 |
|---|---|---|---|---|---|---|---|
| MECHANICAL | Unit | Standard | PEI-1 | PEI-2 | TPU | TPU | TPU |
| Tensile Stress @ Yield, Type I, 5 mm/min | kgf/cm² | ASTM D 638 | — | — | — | 720 | 1020 |
| Tensile Modulus, 5 mm/min | kgf/cm² | ASTM D 638 | — | — | — | 25300 | 37700 |
| Flexural Stress @ Yield, 1.3 mm/min, 50 mm span | kgf/cm² | ASTM D 790 | 16 | 63 | 770 | 1080 | 1560 |
| Flexural Modulus, 1.3 mm/min, 50 mm span | kgf/cm² | ASTM D 790 | 370 | 1520 | 20320 | 27400 | 38700 |
| IMPACT | Unit | Standard | | | | | |
| Izod Impact, notched, 23° C. | cm-kgf/cm | ASTM D 256 | — | — | — | 7.0 | 5.4 |
| PHYSICAL | Unit | Standard | | | | | |
| Specific Gravity | — | ASTM D 792 | 1.12 | 1.16 | 1.19 | 1.24 | 1.30 |
| Melt Flow Rate, 400° C./2.16 kgf | g/10 min | ASTM D 1238 | — | — | — | — | — |
| Melt Flow Rate, 365° C./5.0 kgf | g/10 min | ASTM D 1238 | — | — | — | — | — |
| Melt Flow Rate, 343° C./2.16 kgf | g/10 min | ASTM D 1238 | — | — | — | — | — |
| Melt Flow Rate, 337° C./6.6 kgf | g/10 min | ASTM D 1238 | 9 | 17.8 | — | — | — |
| Melt Flow Rate, 224° C. | g/10 min | ASTM D 1238 | — | — | 17 | 13 | 37 |
| ELECTRICAL | Unit | Standard | | | | | |
| Volume Resistivity | Ohm-cm | ASTM D 257 | — | — | — | 3.00E+16 | — |
| THERMAL | Unit | Standard | | | | | |
| Glass Transition Temperature | ° C. | | — | — | — | — | 147 |
| Heat Deflection Temperature, 1.82 MPa | ° C. | ASTM D 648 | — | — | — | 174 | 160 |

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

What is claimed:

1. A spinal cage for implantation between two adjacent vertebrae, wherein the spinal cage comprises a polymer composition, the polymer composition comprising a polyetherimide, wherein the polyetherimide comprises repeating units of the formula

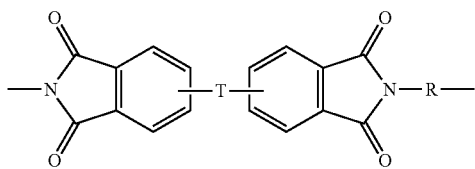

wherein R is a divalent radical of the formula

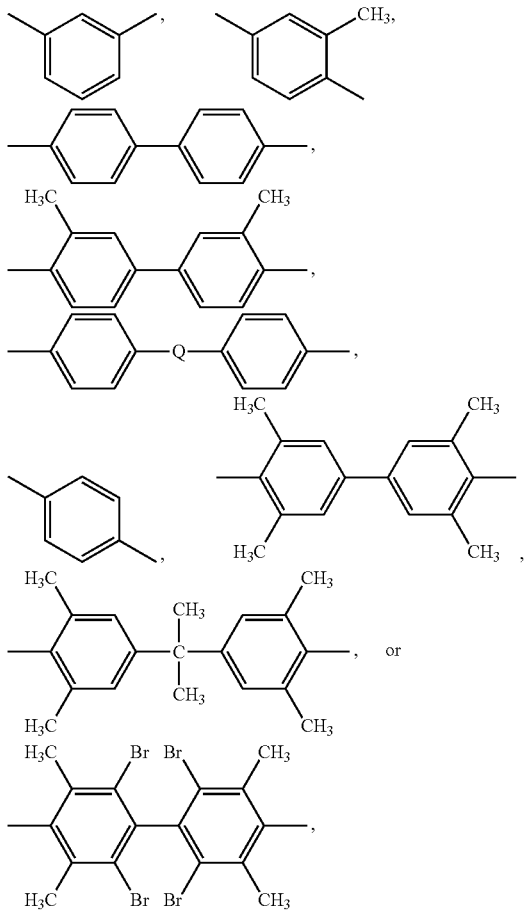

or combinations thereof wherein Q is selected from —O—, —S—, —C(O)—, —SO$_2$—, —SO—, and —C$_y$H$_{2y}$— wherein y is an integer from 1 to 5; and T is —O— or a group of the formula —O—Z—O— wherein the divalent bonds of the —O— or the —O—Z—O— group are in the 3,3', 3,4', 4,3', or the 4,4' positions and Z is a divalent group of the formula

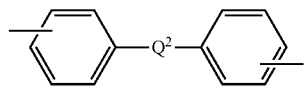

wherein Q$^2$ is selected from —O—, —S—, —C(O)—, —SO$_2$—, —SO—, and —C$_y$H$_{2y}$— wherein y is an integer from 1 to 5.

2. The spinal cage of claim 1, wherein the polyetherimide comprises structural units derived from at least one diamine selected from 1,3-diaminobenzene, 1,4-diaminobenzene, 4,4'-diaminodiphenyl sulfone, oxydianiline, 1,3-bis(4-aminophenoxy)benzene, or combinations thereof.

3. The spinal cage of claim 1, wherein the polyetherimide has a weight average molecular weight of at least about 10,000 to about 150,000 grams per mole (g/mol).

4. The spinal cage of claim 1, wherein the polyetherimide has less than 100 ppm amine end groups.

5. The spinal cage of claim 1, further comprising a biocide, wherein the biocide is selected from germicides, antimicrobials, antibiotics, antibacterials, antiyeasts, antialgals, antivirals, antifungals, antiprotozoals, antiparasites, and combinations thereof.

6. The medical device of claim 1, wherein the spinal cage comprises a polymer component comprising between 40 wt % and 90 wt % of the polyetherimide resin and between 10 wt % and 60 wt % of a filler by weight of the polymer component.

7. The medical device of claim 6, wherein the filler comprises glass, carbon, carbon fiber, or a combination thereof.

8. The spinal cage of claim 1, wherein the polymer composition further comprises ceramic or metal.

9. The spinal cage of claim 1, wherein the spinal cage is sterilized using at least one sterilization process selected from the group consisting of: steam autoclave sterilization, hydrogen peroxide sterilization, gamma-ray sterilization and ethylene oxide sterilization.

10. The spinal cage of claim 1, wherein the spinal cage has a compressive strength after sterilization that is within 5% of the compressive strength of the spinal cage prior to sterilization.

11. A spinal fusion system comprising: a spinal cage and a plate, wherein the plate secures the spinal cage to the vertebrae, wherein the spinal cage comprises a polymer composition, the polymer composition comprising a polyetherimide, wherein the polyetherimide comprises repeating units of the formula

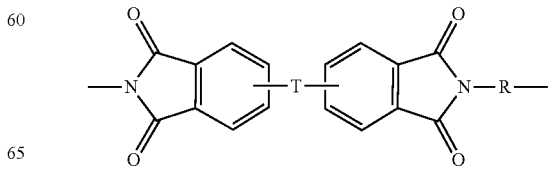

23 wherein R is a divalent radical of the formula

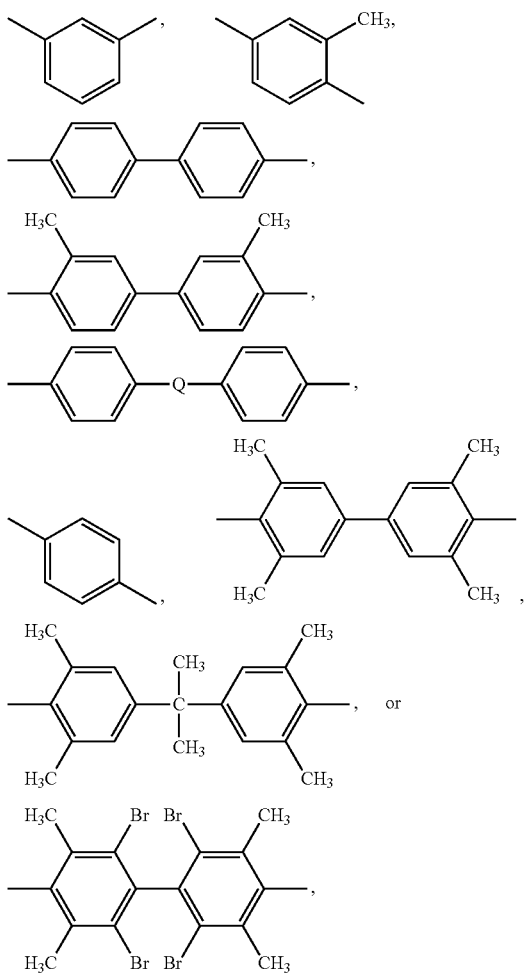

or combinations thereof wherein Q is selected from —O—, —S—, —C(O)—, —SO$_2$—, —SO—, and —C$_y$H$_{2y}$— wherein y is an integer from 1 to 5; and T is —O— or a group of the formula —O—Z—O— wherein the divalent bonds of the —O— or the —O—Z—O— group are in the 3,3', 3,4', 4,3', or the 4,4' positions and Z is a divalent group of the formula

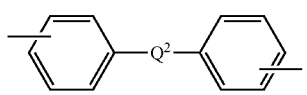

wherein Q$^2$ is selected from —O—, —S—, —C(O)—, —SO$_2$—, —SO—, and —C$_y$H$_{2y}$— wherein y is an integer from 1 to 5.

12. The spinal fusion system of claim 11, wherein the plate comprises polyetherimide.

13. A method of treating a spine of a patient comprising: removing a damaged spinal disk and inserting a spinal cage into an area of the spine that contained the damaged spinal disk, wherein the spinal cage comprises a polymer composition comprising a polyetherimide,

24 wherein the polyetherimide comprises repeating units of the formula

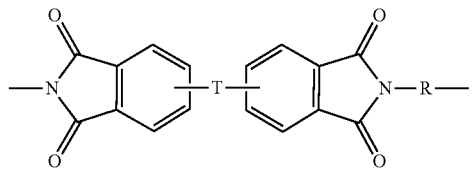

wherein R is a divalent radical of the formula

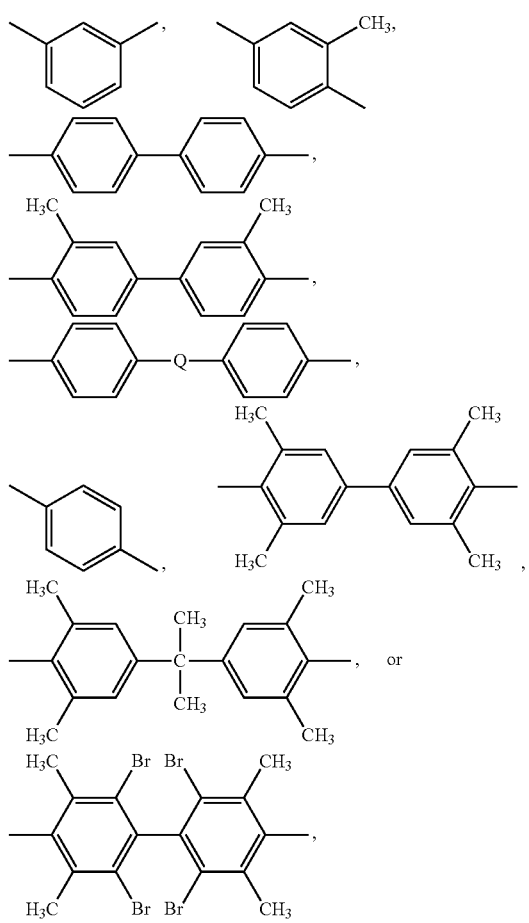

or combinations thereof wherein Q is selected from —O—, —S—, —C(O)—, —SO$_2$—, —SO—, and —C$_y$H$_{2y}$— wherein y is an integer from 1 to 5; and T is —O— or a group of the formula —O—Z—O— wherein the divalent bonds of the —O— or the —O—Z—O— group are in the 3,3', 3,4', 4,3', or the 4,4' positions and Z is a divalent group of the formula

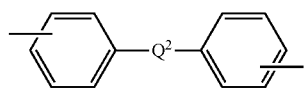

wherein Q$^2$ is selected from —O—, —S—, —C(O)—, —SO$_2$—, —SO—, and —C$_y$H$_{2y}$— wherein y is an integer from 1 to 5.

14. The method of claim 13, wherein the polyetherimide has a weight average molecular weight of at least about 10,000 to about 150,000 grams per mole (g/mol).

15. The method of claim 13, wherein the polyetherimide has less than 100 ppm amine end groups.

16. The method of claim 13, further comprising a biocide, wherein the biocide is selected from germicides, antimicrobials, antibiotics, antibacterials, antiyeasts, antialgals, antivirals, antifungals, antiprotozoals, antiparasites, and combinations thereof.

17. The method of claim 13, wherein the spinal cage comprises a polymer component comprising between 40 wt % and 90 wt % of the polyetherimide and between 10 wt % and 60 wt % of a filler by weight of the polymer component.

18. The method of claim 17, wherein the filler comprises glass, carbon, carbon fiber, or a combination thereof.

19. The method of claim 13, wherein the polymer composition further comprises ceramic or metal.

\* \* \* \* \*